United States Patent [19]

Harvey et al.

[11] 4,356,168

[45] Oct. 26, 1982

[54] OPACIFIED DENTAL CREAM CONTAINING A BINARY FLUORINE-PROVIDING SYSTEM

[75] Inventors: Kenneth Harvey, Wilmslow; Stephen T. Connors, Sale, both of England; Eric Baines, New South Wales, Australia

[73] Assignee: Colgate-Palmolive Company, New York, N.Y.

[21] Appl. No.: 262,013

[22] Filed: May 11, 1981

[51] Int. Cl.³ .................... A61K 7/16; A61K 7/18
[52] U.S. Cl. ................................. 424/52; 424/49
[58] Field of Search ................................. 424/49–58

[56] References Cited

U.S. PATENT DOCUMENTS

| | | | |
|---|---|---|---|
| 3,906,090 | 9/1975 | Colodney | 424/52 |
| 3,911,104 | 10/1975 | Harrison | 424/52 |
| 3,934,000 | 1/1976 | Barth | 424/49 |
| 3,935,304 | 1/1976 | Januszewski et al. | 424/49 |
| 3,937,804 | 2/1976 | Delaney et al. | 424/52 |
| 3,944,661 | 3/1976 | Colodney et al. | 424/49 |
| 4,007,260 | 2/1977 | Kim | 424/52 |
| 4,032,627 | 6/1977 | Suchan et al. | 424/49 |
| 4,036,949 | 7/1977 | Colodney | 424/49 |
| 4,060,599 | 11/1977 | Cordon | 424/49 |
| 4,140,757 | 2/1979 | Wason et al. | 424/49 |
| 4,159,316 | 6/1979 | Januszewski et al. | 424/49 |
| 4,174,387 | 11/1979 | Cordon et al. | 424/52 |
| 4,187,287 | 2/1980 | Schreiber et al. | 424/49 |
| 4,191,742 | 3/1980 | Wason et al. | 424/49 |
| 4,238,476 | 12/1980 | Harvey | 424/52 |
| 4,254,101 | 3/1981 | Denny | 424/52 |
| 4,263,276 | 4/1981 | Harvey | 424/52 |
| 4,264,579 | 4/1981 | Carr | 424/52 |

Primary Examiner—Shep K. Rose
Attorney, Agent, or Firm—Robert L. Stone; Murray M. Grill; Herbert S. Sylvester

[57] ABSTRACT

An opacified dental cream which effects dental remineralization and reduces caries formation. The opacified dental cream contains a binary fluorine providing system which provides fluorine from sodium monofluorophosphate and from sodium fluoride, a synthetic precipitated silica containing up to about 1% by weight of alumina polishing agent and an opacifying agent.

5 Claims, No Drawings

OPACIFIED DENTAL CREAM CONTAINING A BINARY FLUORINE-PROVIDING SYSTEM

FIELD OF THE INVENTION

This invention relates to a dental cream for promoting oral hygiene.

DESCRIPTION OF THE PRIOR ART

In the past dental creams have been used which contain a single fluorine-providing agent such as sodium fluoride, stannous fluoride or sodium monofluorophosphate (it being understood that a minor part of commercial sodium monofluorophosphate includes sodium fluoride).

Recently, as in British Pat. No. 1,435,627 of Beecham Group and U.S. Pat. No. 4,152,719 of Colgate-Palmolive dental creams for promoting oral hygiene have been described which contain two separately added fluorine-providing agents, that is sodium fluoride and sodium monofluorophosphate. However, dental creams containing two such fluorine providing agents and a siliceous polishing material including a small amount of combined alumina have not been described.

It is an object of this invention to provide a dental cream containing sodium fluoride and sodium monofluorophosphate which promotes oral hygiene, for instance by reducing caries formation and by effecting dental remineralisation.

It is a further object to produce a silica abrasive dental cream of high fluorine stability.

SUMMARY OF THE INVENTION

According to the present invention an opaque dental cream comprises 0.5 to 2% by weight of an opacifying agent, a binary fluorine-providing system which provides about 750–1225 ppm fluorine from sodium monofluorophosphate and about 50–1000 ppm fluorine from sodium fluoride and about 15–20% by weight of a polishing agent consisting essentially of a synthetic precipitated silica containing up to about 1% by weight of alumina interbonded therewith.

Sodium monofluorophosphate is employed in amount to provide about 750–1225 ppm fluorine to the dental cream. This corresponds to about 0.5–1% by weight of sodium monofluorophosphate in the dental cream. The preferred amount is about 0.76% which provides about 1000 ppm fluorine to the dental cream.

Sodium monofluorophosphate, $Na_2PO_3F$, as commercially available may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12% preferably above 12.7% a content of not more than 1.5%, preferably not more than 1.2% of free sodium fluoride; and a sodium monofluorophosphate content of at least 12%. preferably at least 12.1% all calculated as fluorine.

Sodium fluoride is separately added to provide an additional fluorine amount of about 50–1000 ppm (for example, 50–100 ppm). This corresponds to about 0.01–0.2% of sodium fluoride.

The polishing material is a synthetic precipitated silica containing up to about 1% by weight of alumina interbonded therewith. Such polishing materials may also be considered to be aluminosilicates, particularly sodium aluminosilicates. Typical examples are described in U.S. Pat. No. 3,906,090 of Colgate-Palmolive and in U.S. Pat. Nos. 4,015,996, 4,105,757 and 4,122,160 of J. M. Huber. Commercially available examples of these materials are ZEO 49 and ZEO 49 B of Huber and TIXOSIL 53 of Sifrance. The polishing agent is employed in amounts of about 15–20% by weight.

If desired a minor amount, such as about 0.5–1%, of dicalcium phosphate may be present as an additional polishing agent.

The dental cream of the invention is opaque. Since the polishing agent is characterized as having a refractive index close to that of humectants such as glycerine and sorbitol which are typically used in dental creams, about 0.5–2% of an opacifying agent such as titanium dioxide or equivalent is employed. The dental cream typically contains about 50–80% by weight of humectant, such as about 20–30% by weight of glycerine and about 30–60% by weight of sorbitol (70% solution).

Other opacifying agents, such as zinc oxide, may be used in orally acceptable amounts which do not adversely react with other constituents of the dental cream.

Water may be present too, in small amounts, such as about 2–7% by weight. If it is desired to colour the dental cream, colouring dyes may be dissolved in the water.

The dental cream also typically includes a gelling agent such as the natural and synthetic gum and gum-like material e.g. Irish moss, gum tragacanth, sodium carboxymethylcellulose, polyvinylpyrrolidone and starch.

Sodium carboxymethyl cellulose is preferred. The gelling agent content is typically about 0.1–5% by weight preferably about 0.1–0.5%. The gelling agent effect can be supplemented with about 7–8% of a filler such as a pyrogenic silica or a silica aerogel. ZEOSYL 200 of J. M. Huber is a desirable silica filler material. "Zeosyl" is a trade mark.

Any suitable surface active or detersive material may be included in the dentifrice compositions. Such compatible materials are desirable to provide additional detersive, foaming and anti-bacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate), higher fatty acid esters of 1,2-dihydroxy propane sulphonate and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides or glycine, sarcosine, alanine, 3-aminopropanoic acid and valine having about 12 to 16 carbons in the acyl group. It is preferred to use the N-lauroyl, myristoyl and palmitoyl sarcoside compounds, however for optimum effects.

The amide compounds may be employed in the form of the free acid or preferably as the water soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine.

The surface active agent is typically employed in amount of about 1–5% by weight, preferably about 1–3% sodium lauryl sulphate is preferred.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and sodium saccharine. Sodium saccharine is preferred. Flavour is typically present in amount of about 0.5–15% by weight, preferably about 1% and sweetener in amount of about 0.1–0.2%.

If desired visible particles of pearlescent flakes, such as titanium dioxide coated mica flakes, may be distributed in the dental cream, typically in amount of about 0.1–0.3% by weight. Likewise, the dental cream may be striped.

The dental cream may be placed in conventional tubes such as lined or unlined aluminium tubes or wax lined lead tubes.

The dental creams should have a pH practicable for use. A pH range of about 5 to 10 is particularly desirable. The reference to the pH is meant to be the pH determination directly on the toothpaste.

DESCRIPTION OF THE PREFERRED EMBODIMENTS

The following Examples are illustrative of the invention. All amounts are by weight unless otherwise specified.

EXAMPLE 1

The following dental cream is prepared by conventional means:

|  | PARTS |
|---|---|
| Glycerol | 25.00 |
| Sorbitol (70%) | 42.31 |
| Sodium Carboxymethyl Cellulose | 0.18 |
| Sodium Saccharine | 0.17 |
| Sodium Monofluorophosphate | 0.82 |
| Sodium Fluoride | 0.02 |
| Water | 3.0 |
| Titanium Dioxide | 0.5 |
| Synthetic precipitated silica containing about 1% combined alumina | 17.0 |
| Zeosyl 200 | 7.0 |
| Dicalcium Phosphate Dihydrate | 1.0 |
| Sodium Lauryl Sulphate | 2.0 |
| Flavor | 1.0 |

EXAMPLE 2

A further dental cream is prepared, again by conventional means, with the formulation of Example 1 save that 0.25 parts of Titanium Dioxide coated mica flakes are added and the water content reduced by the same amount.

Table 1 which appears below, shows formulations of three dental creams which were prepared by conventional means, that identified as Example 3 being in accordance with the present invention. It will be seen that the formulation of Example 3 shows an increased fluorine level and increased fluorine retention over the test period compared with conventional opaque dental creams as exemplified by comparatives A and B.

The fluorine content was determined by the standard method set out by Cropper and Puttnam at p533 of Vol. 21 (1970) of The Journal of the Society of Cosmetic Chemists of Great Britain.

TABLE 1

|  |  | Comparative A | Comparative B | Example 3 |
|---|---|---|---|---|
| Glycerol | | 22.222 | 20.202 | 25.0 |
| Sorbitol (70% solution) | | — | — | 43.05 |
| Sodium Carboxymethyl Cellulose | | 0.9 | 1.1 | 0.2 |
| Sodium Saccharine | | 0.2 | 0.2 | 0.17 |
| Tetrasodium pyrophosphate | | 0.5 | — | — |
| Benzoic acid | | — | 0.2 | — |
| Titanium Dioxide | | — | — | 1.0 |
| Sodium Monofluorophosphate | | 0.76 | 0.76 | 0.76 |
| Sodium Fluoride | | 0.1 | 0.1 | 0.1 |
| Water | | 25.018 | 23.138 | 3.96 |
| Dicalcium phosphate dihydrate | | 48.0 | — | — |
| Alumina (Alcoa C333) | | — | 52.0 | — |
| (synthetic precipitated silica containing about 1% combined alumina) | | | | |
| Zeo 49 | | — | — | 17.0 |
| Syloid 244 | | — | — | 6.0 |
| Sodium Lauryl Sulphate | | 1.5 | 1.5 | 1.76 |
| Flavor | | 0.8 | 0.8 | 1.0 |
| Aging tests: | | | | |
| Soluble fluoritine retention: | | | | |
| Initial | | 0.110 | 0.121 | 0.132 |
| (as % by weight) | 1 month | 0.103 | 0.111 | — |
| | 3 months | 0.093 | 0.104 | 0.140 |
| | 6 months | 0.081 | 0.096 | 0.138 |
| | 1 year | 0.069 | 0.090 | — |
| | 2 years | 0.061 | 0.080 | — |

We claim:

1. An opaque dental cream comprising 2–7% by weight water, 50–80% by weight of humectant, about 0.1–5% by weight of gelling agent, about 7–8% by weight of silica filler supplementing said gelling agent, about 1–5% by weight of surface active agent, 0.5–2% by weight of an opacifying agent selected from the group consisting of titanium dioxide and zinc oxide and mixtures thereof, a binary fluorine-providing system which provides about 750–1225 ppm fluoride from sodium monofluorophosphate and 50–1000 ppm fluorine from sodium fluoride and 15–20% by weight of a polishing agent consisting essentially of a sodium aluminosilicate synthetic precipitated silica containing about 1% of alumina interbonded therewith.

2. A dental cream as claimed in claim 1 wherein the opacifying agent is titanium dioxide.

3. A dental cream as claimed in claim 1 wherein the sodium fluoride provides 50–100 ppm fluorine.

4. A dental cream as claimed in claim 2 containing about 0.5–1% by weight of dicalcium phosphate.

5. A dental cream as claimed in claim 1 containing about 0.1–0.3% of pearlescent titanium dioxide coated mica flakes distributed as visible particles.

* * * * *